(12) United States Patent
Sixto, Jr. et al.

(10) Patent No.: US 6,716,226 B2
(45) Date of Patent: Apr. 6, 2004

(54) SURGICAL CLIP

(75) Inventors: Robert Sixto, Jr., Miami, FL (US);
Juergen A. Kortenbach, Miami Springs, FL (US); Thomas O. Bales, Coral Gables, FL (US)

(73) Assignee: InScope Development, LLC, Miami, FL (US)

( * ) Notice: Subject to any disclaimer, the term of this patent is extended or adjusted under 35 U.S.C. 154(b) by 174 days.

(21) Appl. No.: 09/891,775

(22) Filed: Jun. 25, 2001

(65) Prior Publication Data

US 2002/0198549 A1 Dec. 26, 2002

(51) Int. Cl.⁷ .............................................. A61B 17/08
(52) U.S. Cl. ....................... 606/157; 606/142; 606/158; 606/151; 606/143
(58) Field of Search ................................ 606/157, 142, 606/158, 151, 143

(56) References Cited

U.S. PATENT DOCUMENTS

| 266,632 A | 12/1882 | Danforth | |
|---|---|---|---|
| 4,444,187 A | 4/1984 | Perlin ........................ | 128/346 |
| 5,312,426 A | 5/1994 | Segawa et al. ............. | 606/158 |
| 5,354,306 A | * 10/1994 | Garvey et al. ............. | 606/157 |
| 5,366,459 A | * 11/1994 | Yoon .......................... | 606/151 |
| 5,425,740 A | 6/1995 | Hutchinson ................ | 606/157 |
| 5,441,509 A | * 8/1995 | Vidal et al. ................ | 606/151 |
| 5,464,416 A | * 11/1995 | Steckel ...................... | 606/158 |
| 5,487,746 A | * 1/1996 | Yu et al. .................... | 606/151 |
| 5,522,823 A | 6/1996 | Kuntz et al. ............... | 606/157 |
| 5,632,753 A | 5/1997 | Loeser ....................... | 606/151 |
| 5,741,283 A | 4/1998 | Fahy .......................... | 606/157 |
| 5,993,476 A | 11/1999 | Groiso ....................... | 606/219 |

FOREIGN PATENT DOCUMENTS

GB 2054730 A 12/1981

* cited by examiner

Primary Examiner—John J. Calvert
Assistant Examiner—Robert H. Muromoto, Jr.
(74) Attorney, Agent, or Firm—Gordon & Jacobson, P.C.

(57) ABSTRACT

A surgical clip includes a U-shaped configuration with first and second arms, and a bridge portion therebetween. The first arm is provided with a tip preferably having a catch, and the second arm extends into a deformable retainer having a tissue-piercing end and preferably also a hook. During application, tissue is clamped, and the clip is forced over the clamped tissue and the retainer of the second arm is bent and may be pierced through the tissue. The retainer is toward and around or adjacent the tip of the first arm preferably until the hook is engaged about the catch to secure the clip to the tissue and prevent the clip and tissue from separating. The clip is provided with structure that facilitates the stacking of a plurality of clips in a clip chamber of a clip applier.

4 Claims, 4 Drawing Sheets

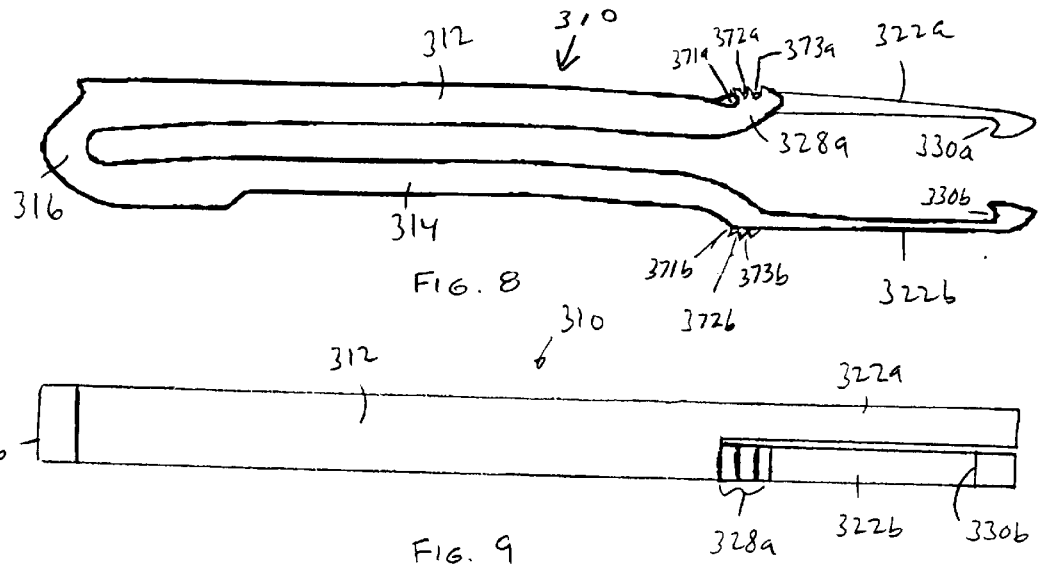
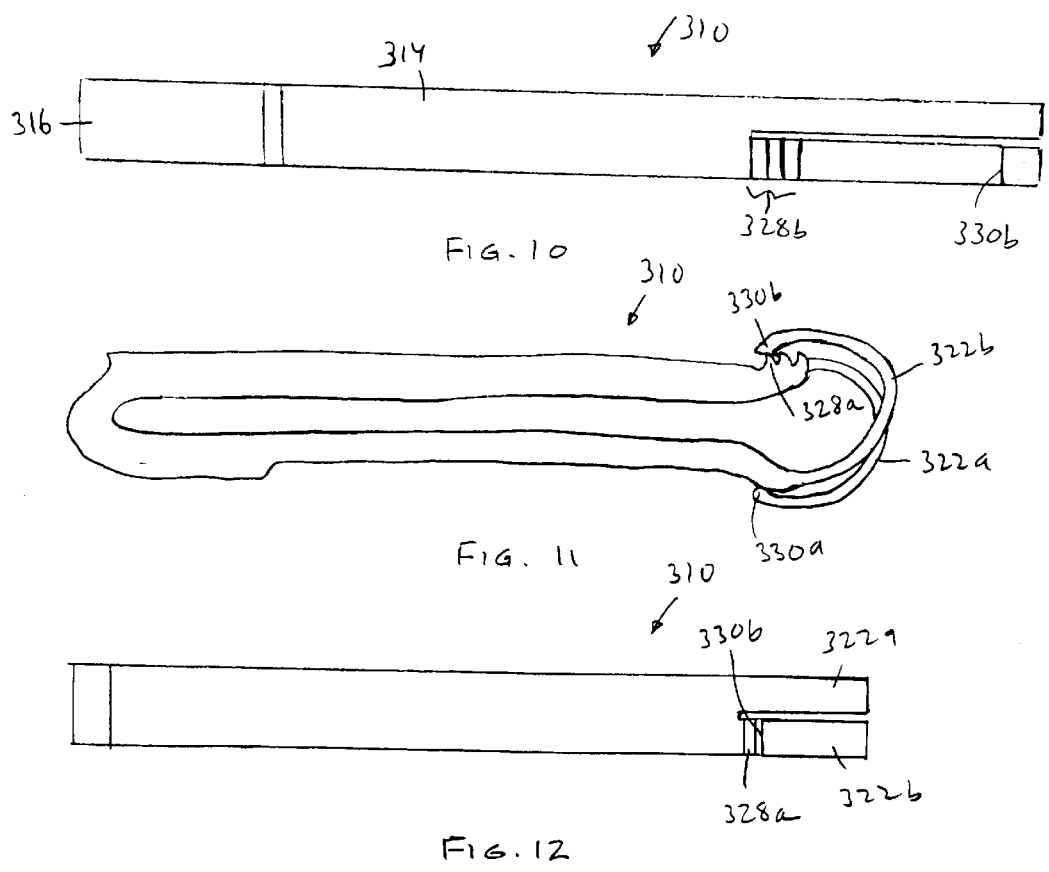

SURGICAL CLIP

BACKGROUND OF THE INVENTION

1. Field of the Invention

This invention relates broadly to surgical devices. More particularly, this invention relates to a surgical clip for clamping and/or suturing, ducts, vessels, and other tissues, for anchoring a tissue, or for attaching a foreign body to a tissue.

2. State of the Art

Surgical clips are generally used to apply clamping force to ducts, vessels, and other tissues. In addition, surgical clips are particularly useful in controlling bleeding of a tissue in lieu of suturing or stapling where suturing or stapling is difficult. However, in certain circumstances, the bleeding tissue is lubricous, and applied clips often slip from the tissue and are dislodged, removing the necessary clamping force thereabout. This is particularly a problem when a clip is provided about tissue which is not a conduit of a size which can be completely surrounded by the clip. For example, it is very difficult to secure a clip about a small peripheral portion of ulcerated stomach tissue and therefore it is difficult to effect hemostasis of such bleeding tissue with a clip. Moreover, the problem is amplified when the clip used is very small.

In order to prevent dislodgement, a combination of a clip and a staple has been described in U.S. Pat. No. 5,522,823 to Kuntz et al. In the Kuntz clip, one end portion of the clip is pierced through the tissue and captured in an eye of another end portion of the clip to secure the clip on the tissue. With the clip piercing the tissue, the likelihood that the clip will become inadvertently dislodged is greatly reduced.

While the Kuntz et al. clip represents a step forward, the disclosed clip is not particularly useful in endoscopic procedures. In particular, both the nature of the clip and the manner in which it is applied are complex. For example, in order to facilitate the bending of the clip through various configurations required of its applier, the clip has portions provided with at least four different widths as well as an eye opening. This complex clip structure is not practical for a clip which is to be used in a flexible endoscopy procedure in which the tools used are of very small diameter, e.g., 2–6 mm (0.08–0.24 inch). In addition, for endoscopic procedures it is highly desirable that multiple clips be able to be applied without removing the clip applier from its general location. The Kuntz et al. clip and applier, however, are not particularly adapted for applying multiple clips, as the Kuntz et al. clip does not stack, and the applier with which it is used holds a single clip at a time.

SUMMARY OF THE INVENTION

It is therefore an object of the invention to provide a surgical clip which remains secured to the tissue to which it is applied.

It is another object of the invention to provide a surgical clip which pierces tissue in order to maintain a secure hold on the tissue to which it is applied.

It is a further object of the invention to provide a surgical clip which is adapted for use in minimally invasive surgery.

It is an additional object of the invention to provide a surgical clip which can be applied in a flexible endoscopy setting.

It is also an object of the invention to provide a surgical clip which can be used with rigid instruments operated through a port in the human body.

It is yet another object of the invention to provide a surgical clip which can be used in open surgery.

It is still a further object of the invention to provide a surgical clip which is relatively easy to manufacture.

It is still another object of the invention to provide a surgical clip which is particularly adapted for use in an applier which holds a plurality of clips.

In accord with these objects, which will be discussed in detail below, a surgical clip is provided having a generally U-shaped configuration with first and second arms, and a bridge portion therebetween. The first arm is provided with a tip preferably having one or more catches, and the second arm extends into a deformable retainer preferably having a tissue-piercing end and preferably also a hook. During application, the clip is forced over compressed tissue. As the clip is forced over the tissue, the retainer of the second arm is bent and may pierce through the tissue. The retainer is preferably sized to be bent sufficiently toward and around the tip of the first arm until the hook engages in one of the catches to secure the clip to the tissue and prevent the clip and tissue from separating. In other embodiments, the clip includes neither the hook nor the catch; the retainer is simply bent to pierce the tissue and preferably folded about the tip of the first arm to prevent the clip and tissue from separating. In yet another embodiment, the clip includes a plurality of retainers which are bent to aid in securing the clip to or about tissue.

According to a preferred aspect of the invention, the clip is provided with structure that facilitates the stacking (or chaining) of a plurality of clips in a clip chamber of an applier. The structure includes: a notch at a junction of the first arm and the bridge portion which is adapted to receive the tip of the first arm of another clip; an elongate recess along the exterior of the second arm which is adapted to receive the retainer of the second arm of another clip; and an interior configuration at the ends of the first and second arms which corresponds to an exterior portion of the bridge portion of another clip. The recess on the second arm may be provided adjacent the bridge portion or between a rear portion of the second arm and the retainer thereof.

Additional objects and advantages of the invention will become apparent to those skilled in the art upon reference to the detailed description taken in conjunction with the provided figures.

BRIEF DESCRIPTION OF THE DRAWINGS

FIG. 8 is a side elevation of a fourth embodiment of a surgical clip according to the invention, shown in a pre-use configuration;

FIGS. 9 and 10 are top and bottom views, respectively, of the fourth embodiment of a surgical clip according to the invention, shown in a pre-use configuration;

FIG. 11 is a side elevation of the fourth embodiment of a surgical clip according to the invention, shown in a post-use configuration; and FIG. 12 is top view of the fourth embodiment of a surgical clip according to the invention, shown in a post-use configuration.

DETAILED DESCRIPTION OF THE PREFERRED EMBODIMENTS

Figure 1:
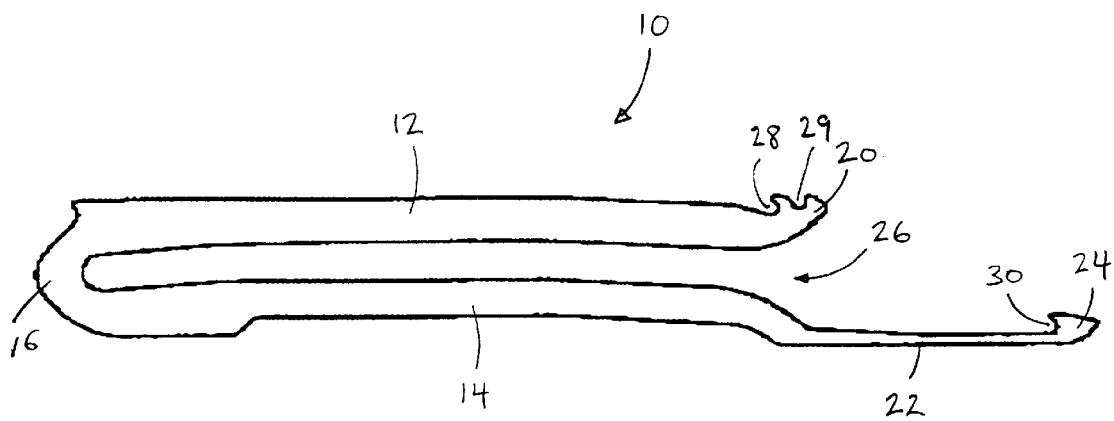
FIG. 1 is a side elevation of a first embodiment of a surgical clip according to the invention, shown in a pre-use configuration.
Figure 2:
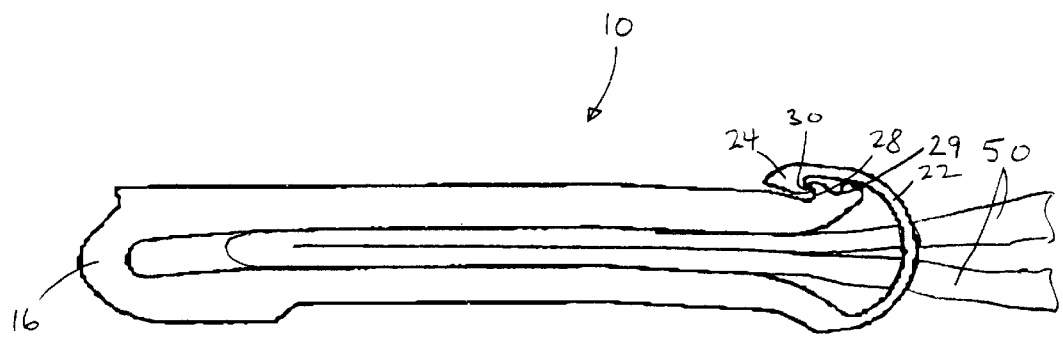
FIG. 2 is a side elevation of the first embodiment of the surgical clip according to the invention shown secured on tissue.

Turning now to FIGS. 1 and 2, a surgical clip 10 includes first and second arms 12, 14, respectively, and a bridge portion 16 therebetween such that the arms and bridge portion are in a generally U-shaped configuration. The first arm 12 is provided with an end 20, and the second arm 14 extends (or transitions) into a deformable retainer 22 preferably having a tissue piercing tip 24. The clip 10 is preferably made from a unitary piece of titanium, titanium alloy, stainless steel, tantalum, platinum, other high Z (substantially radiopaque) materials, nickel-titanium alloy, martensitic alloy, or plastic, although other suitable biocompatible materials may be used. The first and second arms 12, 14 extend in a substantially parallel direction, with the arms and the bridge defining a generally U-shape. The first and second arms 12, 14, as well as the bridge portion 16 are relatively stiff and preferably elastically deformable within the limits of force applied to the arms during use, while the retainer 22 is relatively easily plastically deformable by a clip applier, as briefly described hereafter.

The retainer 22 is sized to be bent across the opening 26 between the first and second arms 12, 14 and about the end 20 of the first arm 12. The retainer preferably has a length 0.7 to 2 times the height of the staple (measured from the outer side of the first arm to the outer side of the second arm). The retainer 22 has a preferred approximate thickness of 0.002–0.020 inch, and preferably tapers down in thickness toward its tip. The overall thickness of an arm is preferably 0.002 inch to 0.080 inch. The overall width of the staple is preferably 0.005 inch to 0.100 inch.

According to a preferred first embodiment, the end 20 of the first arm 12 is provided with one or more catches, e.g., catches 28 and 29, and the tissue piercing tip 24 is provided with a hook 30 which is adapted to engage the catches 28, 29 (FIG. 2).

Figure 3:
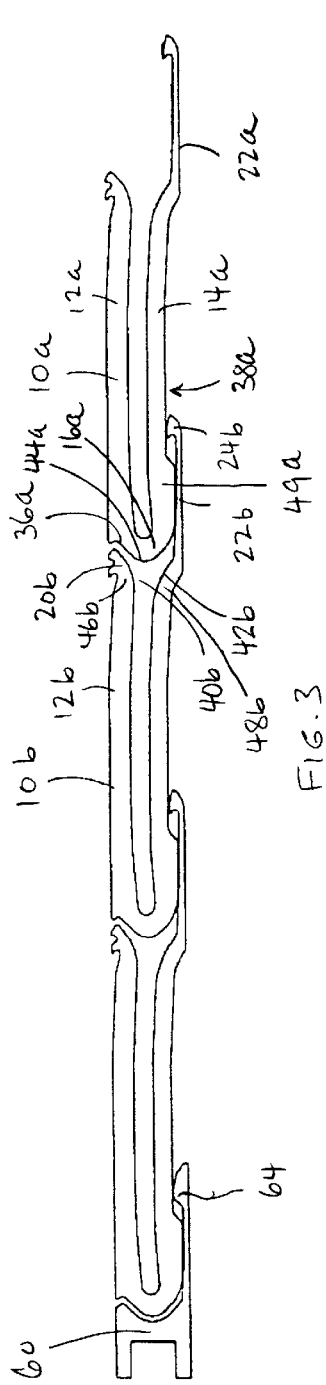
FIG. 3 is a schematic of a plurality of stacked surgical clips according to the invention.
Figure 4:
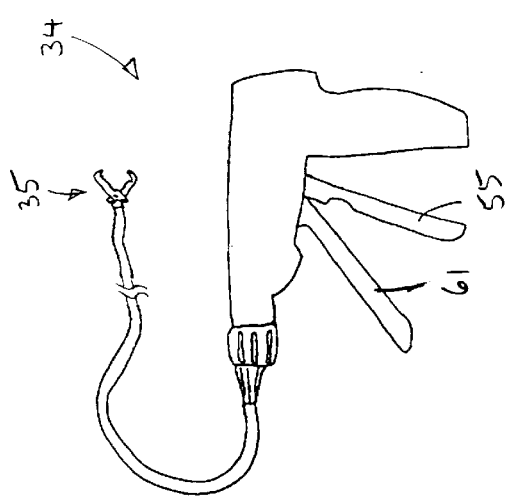
FIG. 4 is a broken side elevation of a flexible endoscopic clip applier used to apply the surgical clips of the invention to tissue.

Referring to FIGS. 1 and 3 (wherein letter subscripts are used to denote like parts on distinct like clips), according to a preferred aspect of the invention, the clip 10 is provided with structure that facilitates the stacking (or chaining) of a plurality of clips in a chamber 33 at the distal end 35 of a clip applier 34 (FIG. 4). The structure includes: a notch 36a at the junction of the first arm 12a and the bridge portion 16a, which is adapted to receive the end 20b of the first arm 12b of a second clip 10b; an elongate recess 38a along the exterior of the second arm 14a, adapted to receive the tip 24b of the retainer 22b of the second arm 14b of the second clip 10b; and an interior portion 40b, 42b of each of the first and second anus 12b, 14b, which has a shape which corresponds to an exterior portion 44a of a bridge portion 16a of a first clip 10a. The corresponding interior portions 40b, 421b are preferably defined by slight outward bends 46b, 48b, or an internal flaring, in the first and second arms. According to the first embodiment, the recess 38a is located between a rear portion 49a of the second arm 14a and the retainer thereof.

Figure 5:
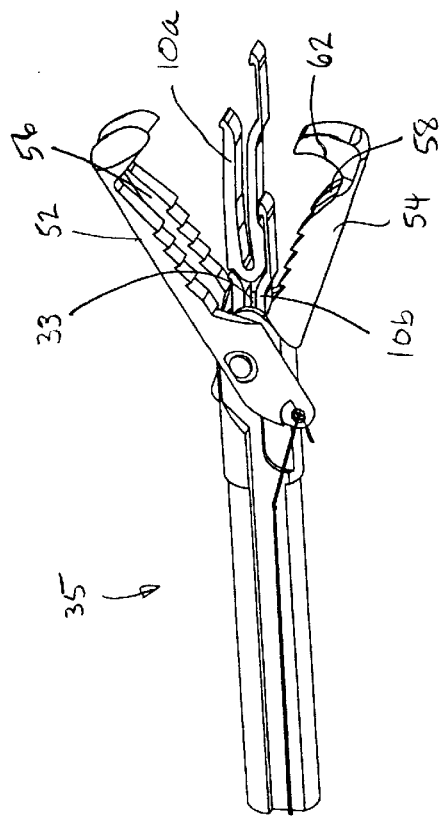
FIG. 5 is an enlarged partial section of the distal end of the clip applier of FIG. 4.

Referring to FIGS. 4 and 5, the clips are particularly suitable for use in a flexible endoscopic clip applier (although they may be used in rigid instruments in both laparoscopic and open surgery), as the clips may be manufactured in the small sizes necessary for such minimally invasive procedures, e.g., 0.04–0.08 inch (1–2 mm) across the first and second arms. Prior to use, a plurality of clips, e.g., 10a, 10b, are positioned in the above described stacked configuration in the chamber 33 of the clip applier 34. During application, and referring to FIGS. 2, 4 and 5, the jaws 52, 54 of the clip applier 35 are clamped (by operation of a first handle 55) about the tissue 50 over which the cup 10a is to be applied. The tissue is thereby compressed. The jaws 52, 54 include grooves 56, 58 through which the arms 12, 14 of a clip can be pushed. With the tissue compressed by the jaws, the clips are pushed distally by an arm 60 (FIG. 3) at the rear of the chamber 33 until the arms 12a, 14a of the distalmost clip 10a are forced over the compressed tissue. The arm 60 is attached to a pushwire, coil, tube, or other structure (not shown) which is moved relative to the chamber 33 by a second handle 61 on the clip applier (FIG. 54). As the clip 10 is pushed through the grooves 56, 58 over the tissue 50, the retainer 22 of the second arm 14 contacts an anvil 62 at the end of jaw 54 which bends (plastically deforms) the retainer and pushes the retainer toward and around (or at least adjacent) the end 20 of the first arm, preferably until the hook 30 of the tip 24 is engaged about a catch, e.g, catch 28, to secure the clip to the tissue 50 (FIG. 2). If the clip is provided over a portion of tissue which, as a whole, is relatively larger than the space between the arms of the clip, as the retainer is bent by the anvil it will likely pierce the tissue. As the arms 12, 14 and bridge 16 are relatively stiff the arms and bridge retain their shape and are not plastically deformed during application over tissue. That is, any expansion of the clip between the arms is minimal and elastic.

After a clip is deployed, the other clips in the chamber are preferably retracted back into the chamber to reset the clip applier in preparation for subsequent clip application. The recess 38 on the clips provides a structure by which the clips may be engaged and maneuvered proximally within the chamber via a retention portion 64 of the arm 60 (FIG. 3).

Figure 6:
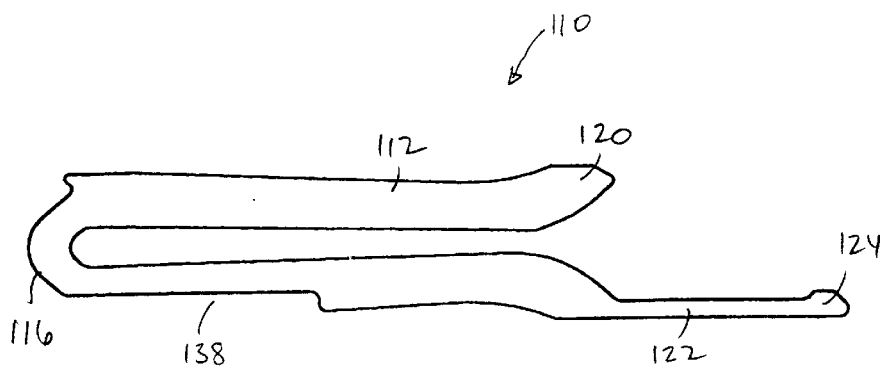
FIG. 6 is side elevation of a second embodiment of a surgical clip according to the invention, shown in a pre-use configuration.

Turning now to FIG. 6, a second embodiment of the surgical clip 110, substantially similar to the first embodiment (with like parts having numbers incremented by 100), is shown. The end 120 of the first arm 112 of the clip 110 does not include a defined catch, although it does extend outwardly. The tip 124 of the retainer 122, consequently, does not include a hook, but preferably is enlarged. When the retainer 122 is bent about the end of the first arm, the enlarged tip 124 rests against the back of the outwardly extending end 120. When the retainer 122 is bent or folded over the end of the first arm 112, approximately 0.3–1.0 1b of force (for relatively small clips) is required to straighten (i.e., plastically deform) the clip from its closed configuration. In addition, the recess 138 on the second arm is provided adjacent the bridge portion 116 and permits stacking of like clips. Providing the recess 138 in such a manner permits a mechanism (not shown) on a clip applier to apply distal force to a clip or clip stack within a clip chamber, but does not facilitate proximal movement of the clip or stack via engagement at the recess.

Figure 7:
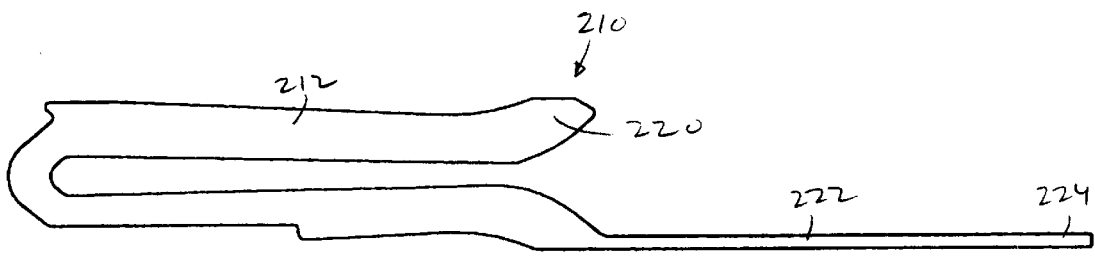
FIG. 7 is side elevation of a third embodiment of a surgical clip according to the invention, shown in a pre-use configuration.

Turning now to FIG. 7, a third embodiment of the surgical clip 210, substantially similar to the first embodiment (with like parts having numbers incremented by 200), is shown. The tip 224 of the retainer 222 does not include any enlargement, but is rather designed to be partially bent to pierce the tissue and then be further bent substantially about the end 220 of the first arm 212 in order to secure the clip on tissue.

Turning now to FIGS. 8 through 10, a fourth embodiment of the surgical clip 310, substantially similar to the first embodiment (with like parts having numbers incremented by 300), is shown. The clip 310 includes first and second arms 312, 314 and a bridge 316, as in the previous embodiments. The first arm 312 includes both a catch portion 328a and a retainer portion 322a. The second arm 314 also includes both a catch portion 328b and a retainer portion 322b. The retainer and catch portions are offset such that retainer portion 322a is adapted to be bent toward catch portion 328b, with the hook 330a engaging the catch portion, and retainer portion 322b is adapted to be bent toward catch portion 328a for similar engagement. The catch portions 328a, 328b are shown with three catches 371a, 372a, 373a and 371b, 372b, 373b, respectively. Multiple catches facilitate a locked closing in different positions.

Such a clip is deployed in the same manner as the clip of the first embodiment, but the jaw assembly of the clip applier includes anvils at the ends of both of the jaws (not shown) to effect the bending and folding of the retainer portions 322a, 322b. In this manner, the hooks 330a, 330b at the end of the retainer portion engage the catch portions 328a, 328b, as shown in FIGS. 11 and 12.

While the clips are described as being adapted to pierce tissue, it is recognized that the clips may be applied over a duct, vessel, or other conduit or tissue which the clips completely surrounds such that the clips are clamped thereon but do not pierce the tissue thereof. In such use, the clamping force of the clips retains the clips over the tissue. Furthermore, the clips can be used to clamp a first tissue and pierce a second tissue to secure the first and second tissues together, e.g., as in a stitch. Moreover, the clips can be used to attach a foreign body to tissue.

There have been described and illustrated herein several embodiments of a surgical clip and a method of using the same. While particular embodiments of the invention have been described, it is not intended that the invention be limited thereto, as it is intended that the invention be as broad in scope as the art will allow and that the specification be read likewise. Thus, while the clip is particularly adapted for manufacture in the small size necessary for flexible endoscopy, it will be appreciated that the clip may be made in other sizes as well. In addition, while in one embodiment the retainer tip includes a hook and the end of the first arm is provided with a catch, it will be appreciated that the retainer tip may have a catch and the first arm may have a hook. In addition, other engagement means may be used. Also within the scope of the invention are other clip configurations with more than two retainers, and preferably more than two catches. The retainers and catches may be provided on the same arm, or alternatively, all the retainers may be on one arm, while all the catches are all provided on the other arm. Furthermore, in a multi-retainer embodiment, it is not necessary to have any catches, as described with respect to the second and third embodiments. It will therefore be appreciated by those skilled in the art that yet other modifications could be made to the provided invention without deviating from its spirit and scope as claimed.

What is claimed is:

1. A surgical clip, comprising:
   a) a first arm portion having a tip and a first opposite end,
   b) a second arm portion having a retainer and a second opposite end; and
   c) a bridge portion connecting the first and second opposite ends, wherein a notch is provided at a junction of said first arm and said bridge portion, an elongate recess is provided along an exterior of said second arm, and an interior portion of each of said first and second arms has a shape which corresponds to an exterior portion of said bridge portion.

2. A surgical clip according to claim 1, wherein:
   said recess is located between a central portion of said second arm and said retainer.

3. A surgical clip according to claim 1, wherein:
   said recess is provided adjacent said bridge portion.

4. An arrangement of surgical clips, comprising:
   a) a first surgical clip having,
      i) a first arm portion having a tip and a first opposite end,
      ii) a second arm portion having a retainer extending therefrom and a second opposite end, and
      iii) a bridge portion connecting the first and second opposite ends, wherein a notch is provided at a junction of said first arm and said bridge portion, an elongate recess is provided along an exterior of said second arm, and an interior portion of each of said first and second arms has a shape which corresponds to an exterior portion of said bridge portion; and
   b) second and third surgical clips substantially similar to said first surgical clip, wherein, when said first surgical clip is stacked on said second surgical clip and said second surgical clip is stacked on said third surgical clip, said notch of said first surgical clip is adapted to receive said tip of said first arm of said second surgical clip, said recess of said first surgical clip is adapted to receive said retainer of said second arm of said second surgical clip, and said interior portion of said first and second arms of said third surgical clip is adapted to receive said exterior portion of said bridge portion of said second surgical clip.

* * * * *